(12) United States Patent
Taylor et al.

(10) Patent No.: US 7,363,168 B2
(45) Date of Patent: Apr. 22, 2008

(54) ADAPTIVE BASELINE ALGORITHM FOR QUANTITATIVE PCR

(75) Inventors: Roger Taylor, San Diego, CA (US); Alan Ridgeway Orr, San Diego, CA (US)

(73) Assignee: Stratagene California, La Jolla, CA (US)

( * ) Notice: Subject to any disclaimer, the term of this patent is extended or adjusted under 35 U.S.C. 154(b) by 388 days.

(21) Appl. No.: 10/262,474

(22) Filed: Oct. 1, 2002

(65) Prior Publication Data

US 2003/0148332 A1    Aug. 7, 2003

Related U.S. Application Data

(60) Provisional application No. 60/346,812, filed on Oct. 19, 2001, provisional application No. 60/326,620, filed on Oct. 2, 2001.

(51) Int. Cl.
*G06F 7/00* (2006.01)

(52) U.S. Cl. ............................ 702/19; 702/20; 703/11; 435/6

(58) Field of Classification Search ................. 702/19; 435/91.2
See application file for complete search history.

(56) References Cited

U.S. PATENT DOCUMENTS 5,710,381 A * 1/1998 Atwood et al. .......... 73/864.91
6,783,934 B1 * 8/2004 McMillan et al. ............. 435/6

OTHER PUBLICATIONS

Merriam-Webster On-Line Dictionary, available at http://www.m-w.com/cgi-bin/dictionary?book=Dictionary&va=adaptation, accessed Jun. 6, 2005.*
Merriam-Webster On-Line Dictionary, available at http://www.m-w.com/cgi-bin/dictionary, accessed Jun. 6, 2005.*
International Search Report of International Application No. PCT/US02/31144.
Leverkoehne Ina et al., Real-Time RT-PCR Quantitation Of MCLCA1 and MCLCA2 Reveals Differentially Regulated Expression In Pre-And Postnatal Murine Tissues, *Histochemistry and Cell Biology*, vol. 118, No. 1, Jul. 2002, pp. 11-17, XP002323027 ISSN: 0948-6143.
Supplementary European Search Report regarding EP 02763814.
Pfaffi, "A new mathematical model for relative quantification in real-time RT-PCR"; Nucleic Acids Research, 2001, vol. 29, No. 9 e45.

* cited by examiner

*Primary Examiner*—Mary K Zeman

(57) ABSTRACT

The invention relates to baseline subtraction algorithms developed to reduce tube-to-tube and cycle-to-cycle variabilities during real time PCR amplification. Particularly, the invention relates to algorithms for determining the threshold cycle for the first reliable detection of the amplified nucleic acid product. The invention also relates to computer programs comprising the algorithm and methods and/or systems implementing the algorithm.

22 Claims, 16 Drawing Sheets

[A]

Amplification plots from a dilution series of B7 detected with FAM beacon: these are fluorescence.

[B]

| | |
|---|---|
| Manufacturer: | Dell |
| Series: | Desktop or Mini Tower |
| Processor: | Pentium 4 at 1.6GHz (minimum speed offered) |
| Memory: | 256MB SDRAM (minimum speed offered) |
| Keyboard: | Dell QuietKey Keyboard |
| Monitor: | 16 inch Flat Panel Monitor (Dell or Other) |
| Hard Drive: | 20GB (minimum speed offered) |
| Floppy Drive: | 3.5 inch |
| Mouse: | MS IntelliMouse |
| Network Card: | Integrated Intel or 3COM 10/100 Ethernet Controller |
| Modem: | None |
| CD-ROM Drive: | CD-RW Drive (minimum speed offered) |
| Sound Card: | Integrated Audio |
| Speakers: | Integrated Speakers |
| Operating System: | Microsoft Windows 2000 |
| Bundled Software: | Microsoft Office 2000 Small Business or XP Small Business |
| Antivirus: | Norton Antivirus |
| Product Support: | Minimum or no service (1 year parts acceptable) |
| Power Protection: | Internet Office 280 UPS System, see Sheet 2 of 2. |

PURCHASE SPECIFICATION

3. PROCUREMENT:
  3.1 MANUFACTURING (OR ENGINEERING) REVIEWS THE SPECIFICATIONS AND VERIFIES VIA THE "DELL" WEBSITE, WWW.DELL.COM.
  3.2 MANUFACTURING (OR ENGINEERING) BEGIN THE ORDER PROCESS ON "DELL'S" WEBSITE AND ADVISES PURCHASING.
2. VERIFY SPECIFICATIONS WITH MANUFACTURING (OR ENGINEERING) PRIOR TO PROCUREMENT.
1. SOURCE: DELL

NOTE:

FIGURE 12A

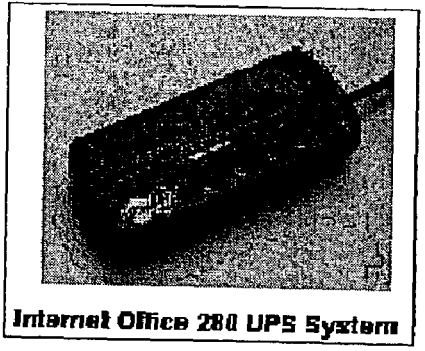

Internet Office 280 UPS System

| UPS type | Small format standby UPS protects connected equipment from blackouts, brownouts, overvoltages, surges and line noise. Includes modem line surge protection and surge suppression only outlets |
|---|---|
| Input/output voltage | 120 |
| Input/output frequency | 60/80 |
| Output VA | 280 |
| Output watts | 100 |
| On-line waveform | Pure sine |
| On battery waveform | PWM sinusoidal |
| Voltage regulation | Output voltage in battery mode is regulated to 120 volts +/-5% |
| Full load runtime (min.) | 4 |
| ½ load runtime (min.) | 10 |
| Typical runtime (PC w/ 15" mon.) | up to 11 min. |
| External battery compatible | Not supported. See selected Smart XL, RM and Datacenter models for this capability |
| Recharge rate to 8046 (hours) | 2-4 |
| Transfer time (milliseconds) | 2-4 |
| Suppression joule rating | 240 |
| Maximum surge current (amps) | 19,500 |

SUBSTITUTE FIGURE 12B

ADAPTIVE BASELINE ALGORITHM FOR QUANTITATIVE PCR

RELATED APPLICATIONS

The present application claims the benefit of U.S. provisional application with Ser. No. 60/326,620, filed Oct. 2, 2001 and U.S. provisional application with Ser. No. 60/346,812, filed Oct. 19, 2001, the entirety of each is incorporated herein by reference.

FIELD OF THE INVENTION

The invention is related to baseline subtraction algorithms, methods of using the same, and a system and computer program product for implementing the same.

BACKGROUND

Polymerase Chain Reaction (PCR) is a powerful technique commonly used in today's laboratories for specific amplification and detection of as little as a single copy of a target nucleic acid sequence. PCR also is used for the quantification of nucleic acid sequences because of the quantitative relationship between the amount of starting target sequence and the amount of PCR product at any given cycle.

End-point PCR is widely used in applications for amplifying nucleic acid templates. In end-point PCR, a template is added at the beginning of a PCR reaction and the reaction is carried out in multiple cycles, usually 20 to 50 cycles. It is the end product of the amplification reaction which is detected and/or quantified. In contrast, real time quantitative PCR (QPCR) monitors the progress of a PCR amplification as it is occurring. In real-time QPCR techniques, signals (generally fluorescent) are monitored as they are generated. The number of cycles required to achieve a chosen level of fluorescence varies directly with the concentration of amplifiable targets at the beginning of the PCR process, enabling a measure of fluorescent intensity to provide a measure of the amount of target DNA in a sample. Fluorescence intensities are detected during the annealing/extension period of each PCR cycle and the output of this detection is fed to a processor for storage and data manipulation. End-point PCR is less accurate than QPCR because the measurement is made later in the PCR, which means more variables have had the opportunity to affect the results. For example, as reaction components are depleted, amplification is reduced. Different signal levels at endpoint might be caused by slight differences in limiting reagents rather than starting targets. This limitation is less severe early in a PCR reaction.

The data obtained during amplification is normalized by the processor which identifies a baseline of background signals (the expected signal in a PCR tube in the absence of a target nucleic acid) and which removes background signals from observed signals. The result of baseline subtraction is a measure of signal intensity which more accurately reflects the amount of target nucleic acid in a sample. Baseline subtraction calculations generally set the background signal observed in a tube during the cycles before amplification as the baseline. The range of cycles before amplification occurs is defined by endpoints (e.g., start and ending cycles) set by the user. Typical guidelines for selecting starting and ending cycles provide that the starting cycle is chosen after the typical variability in the first few cycles has abated and the ending cycle is chosen before amplification has occurred in any tube. Typically, signal obtained from these cycles is fitted with a line using a least mean squares algorithm. This best fit line is used to predict the background for all the cycles of a QPCR experiment, which is then subtracted from data generated from each sample which is being evaluated (see, e.g., as described in U.S. Pat. No. 5,928,907).

This system of setting a range for the calculation of a best-fit line has some limitations: 1) if samples with different starting quantities are used, then the best choice for the last endpoint will differ from sample to sample; 2) different users (or the same user at different times) can choose different endpoints; and 3) the same experiment analyzed with different endpoints will give a different result.

Inconsistency in baseline subtraction can cause larger errors in the final determination of unknown starting copies.

SUMMARY OF THE INVENTION

There is a need in the art for an adaptive baseline subtraction algorithm that reduces the effects of tube-to-tube variabilities which occur during quantitative PCR amplification.

In one aspect, the invention provides a method for calculating an adaptive baseline for a plurality of sample wells in a sample block cycling through cycles of a PCR reaction. The method comprises plotting intensity of actual optical signal observed in a well as a function of cycle number for that well to obtain a first plot, determining a starting cycle and an ending cycle for the well, and fitting points between and including the starting and ending cycle to a line to determine the best fit between the points and the line. However, in one aspect, a non-linear function is used for determine the best fit. The best fit obtained for the well is used to establish the baseline for that well. The steps of plotting intensity, determining the starting and ending cycle, determining the best fit, and establishing the baseline are performed individually for each of the plurality of wells.

In one aspect, the step of determining the starting cycle and ending cycle comprises obtaining a 3-point moving average of the intensity of actual signals obtained for each cycle starting from cycle 2 and plotting said 3-point moving average as a function of cycle number starting from cycle 2 to obtain a second plot.

In another aspect, a Cycle X is identified from the first or second plot. Cycle X has a maximum change of slope from its previous cycle and has four immediately subsequent cycles, each having an increased slope compared to its previous cycle. In one aspect, Cycle X is identified within the first 8 cycles of the PCR reaction and an ending cycle is identified which is three cycles, or two cycles, or one cycle before Cycle X. However, in another aspect, Cycle X is not identified within first 8 cycles of the PCR reaction. In this aspect, Cycle X is assigned as the ending cycle.

In a further aspect, the starting cycle is selected from the group consisting of: a first cycle which shows a different slope trend from its previous cycle; a cycle having a positive slope which is greater than the slope of its previous cycle; and a cycle having a slope less than 10% of an initial slope.

In one aspect, the best-fit line is calculated using a standard least root-mean-square-error algorithm:

$$rmse = \sqrt{\frac{\sum_{i=S}^{E}(m \times i + b) - y_i}{N}},$$

wherein N is the number of cycles between said starting and said ending cycles; S is said starting cycle; E is said ending cycle; $y_i$ is a signal of an $i^{th}$ cycle; and m and b are parameters of said best fit line.

In another aspect, at least one of the sample wells in the sample block comprises a sample suspected of containing a template nucleic acid and the optical signal is from a label (e.g., such as a fluorescent label) specific for the nucleic acid. In a further aspect, the method comprises the step (d) of subtracting the adaptive baseline calculated for the at least one of the wells from a first plot plotted for the at least one well to generate an adapted signal plot. Preferably, the adapted signal plot is compared to a first standard plot generated from a PCR reaction comprising a known amount of template concentration. Still more preferably, the standard plot has been adjusted to remove a baseline. The comparing can be used to determine the amount of template in the sample.

The invention also provides a computer program product comprising program instructions for performing the method described above.

The invention further provides a system for calculating an adaptive baseline for a PCR reaction. The system comprises an analyzing device comprising a memory for implementing the program instructions of the computer program product described above. In one aspect, the system further comprises a thermocycler for receiving the sample block, an input device (e.g., a detector) for collecting optical signals from the sample wells of the sample block, and an output device (e.g., such as a computer) for displaying data obtained by or generated by the analyzing device.

BRIEF DESCRIPTION OF DRAWINGS

The object and features of the invention can be better understood with reference to the following detailed description and drawings.

FIG. 12A is an example of an analyzing device according to one embodiment of the invention.

FIG. 12B is another example of an analyzing device according to one embodiment of the invention.

DETAILED DESCRIPTION OF THE INVENTION

Figure 1:
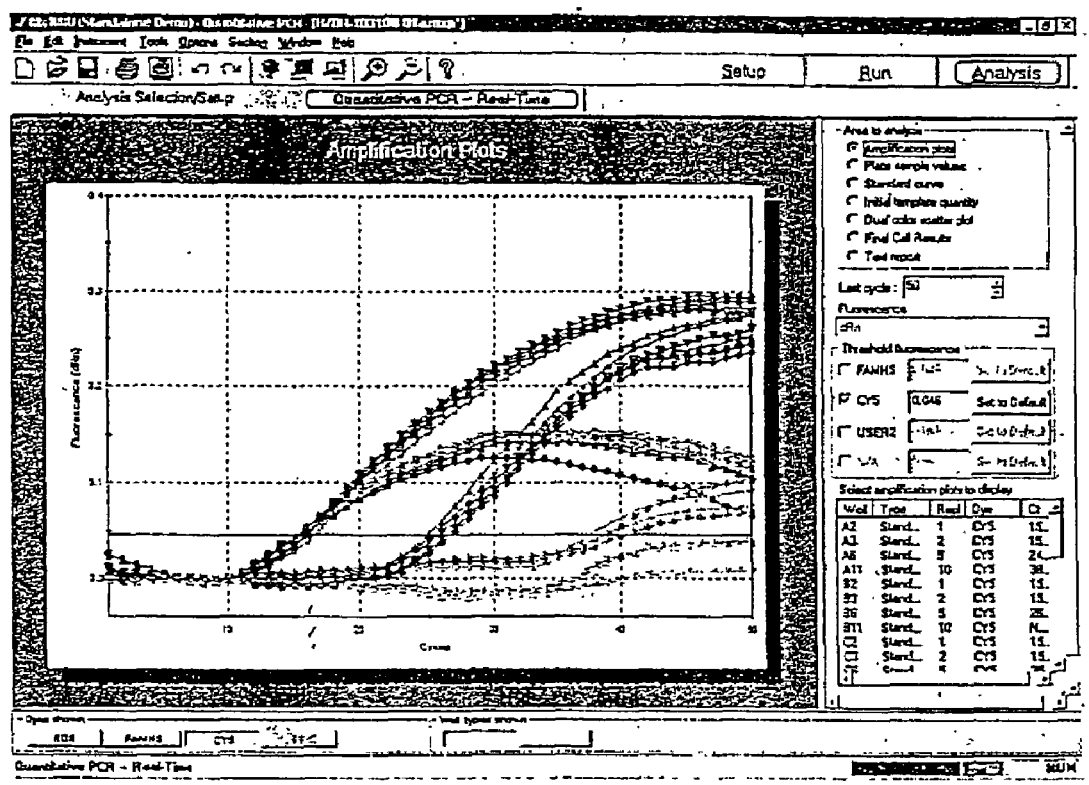
FIG. 1 is a graph showing a PCR amplification reaction calculated with a baseline using fixed starting and ending cycles for 4 samples according to one embodiment of the invention.
Figure 2:
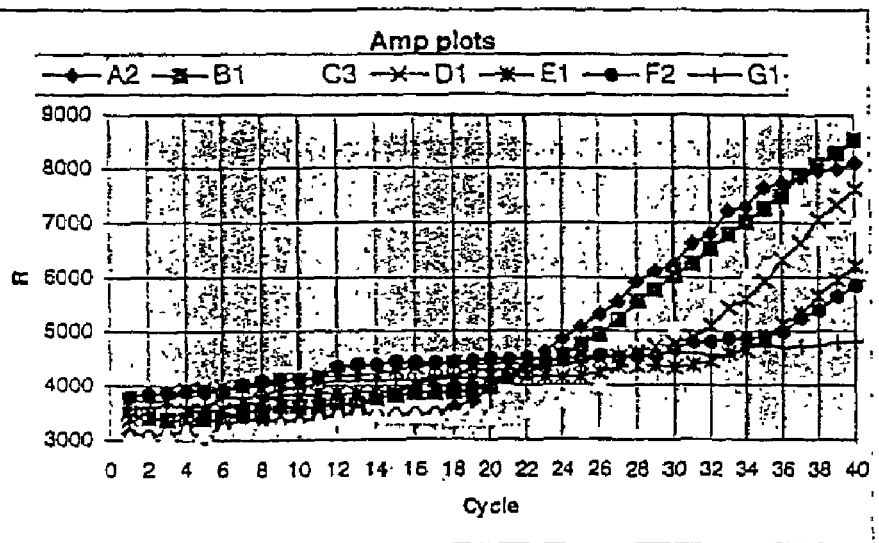
FIG. 2A is a graph showing the actual amplification signal plot as a function of cycle number according to one embodiment of the invention.
FIG. 2B is a graph showing the root mean square error ("rmse") calculation of the difference between the measured value and the predicted value of the signal at each cycle of a PCR reaction using data in FIG. 2A according to one embodiment of the invention.
FIG. 2C is a graph showing another PCR amplification reaction calculated with a baseline using fixed starting and ending cycles for 4 samples according to one embodiment of the invention. Many samples have data below 0 before the signal rises enough to be detected.
FIG. 2D is a graph showing the PCR amplification calculated with an adaptive baseline for the same 4 samples used in FIG. 2C according to one embodiment of the invention. The endpoints are selected independently for each sample and there are fewer below-zero data points before the amplification can be detected.
Figure 2:
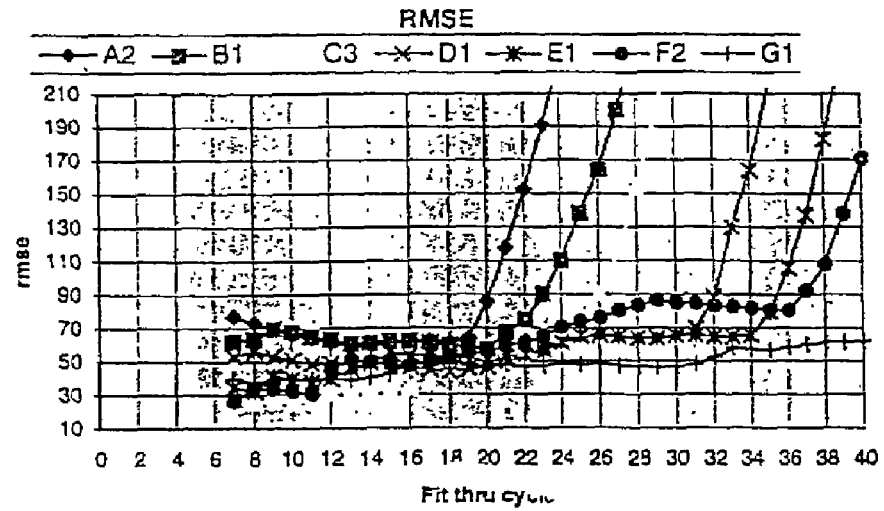
Figure 2C:
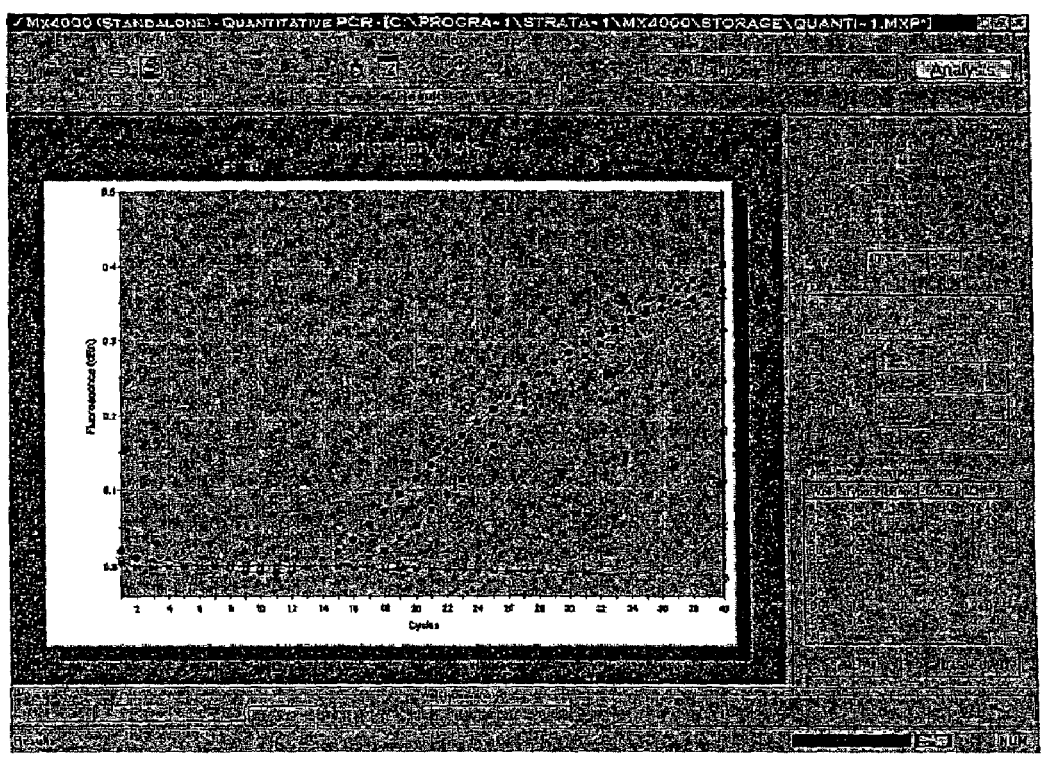
Figure 2D:
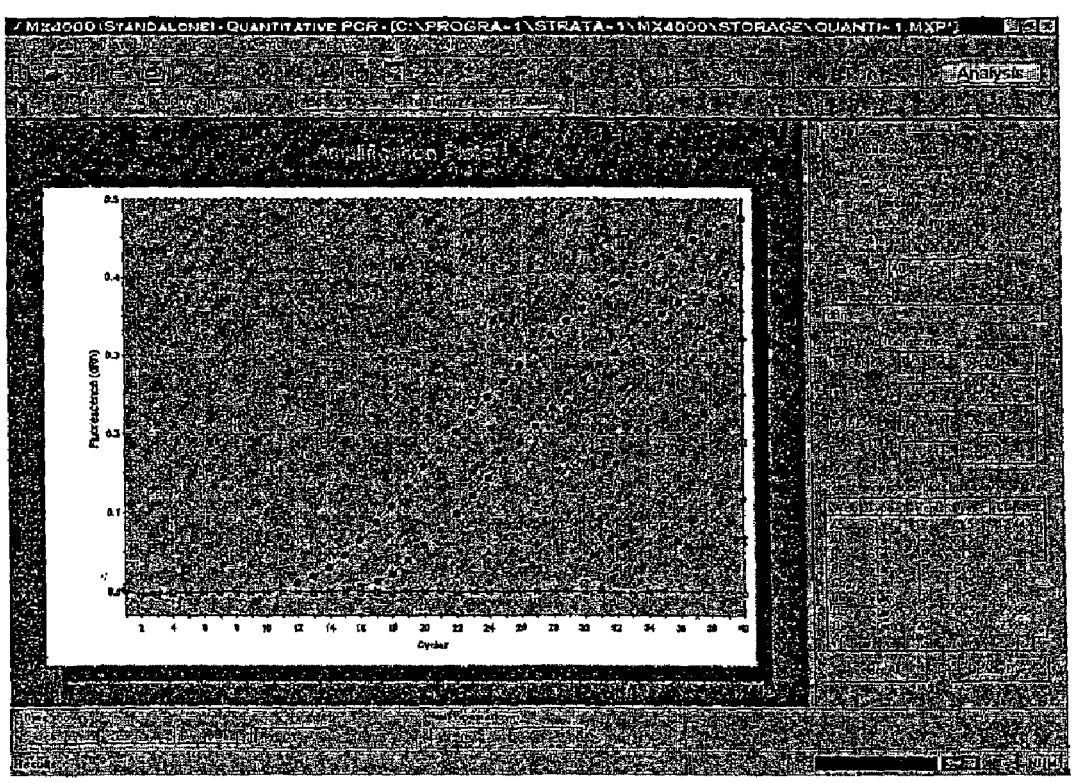
Figure 3:
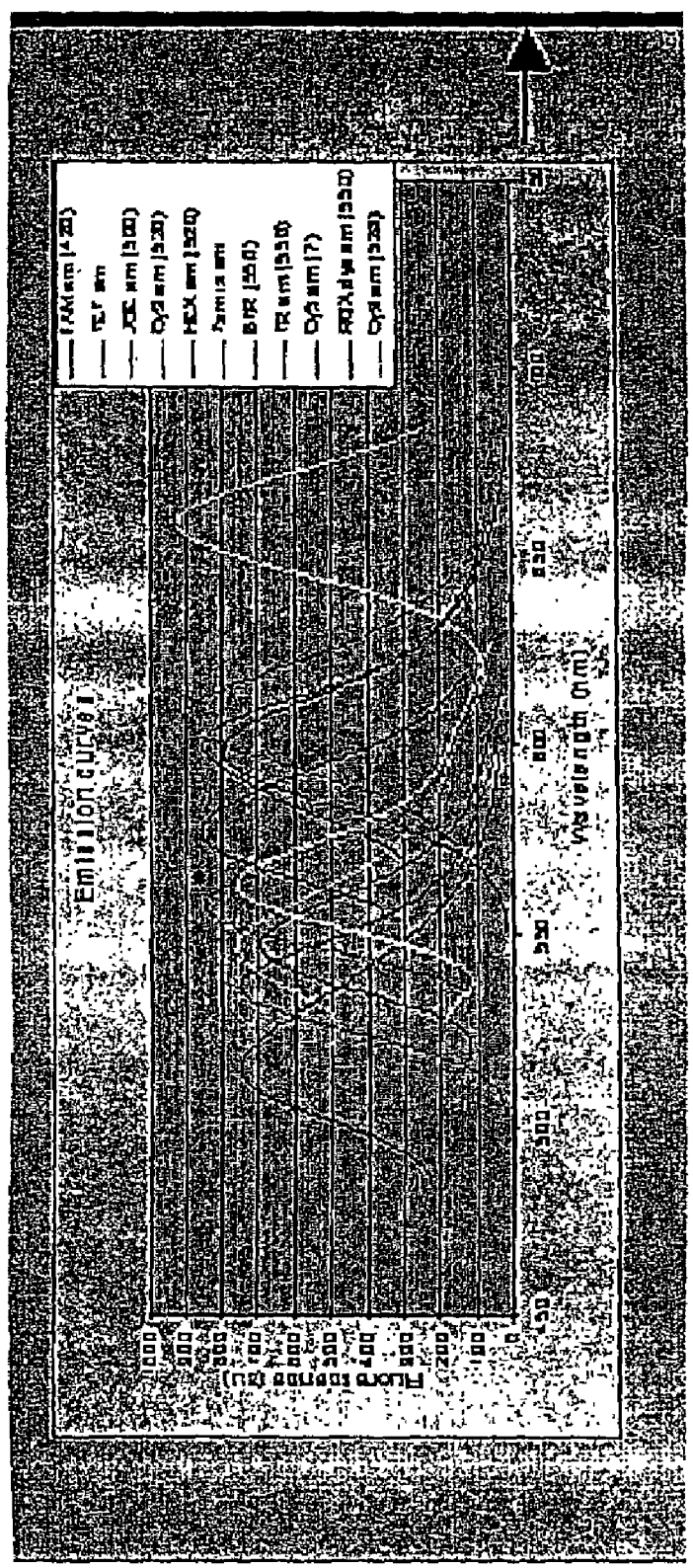
FIG. 3. Detection of fluorescent signals with emission wavelengths ranging from 350-830 nm according to one aspect of the invention.
Figure 4:
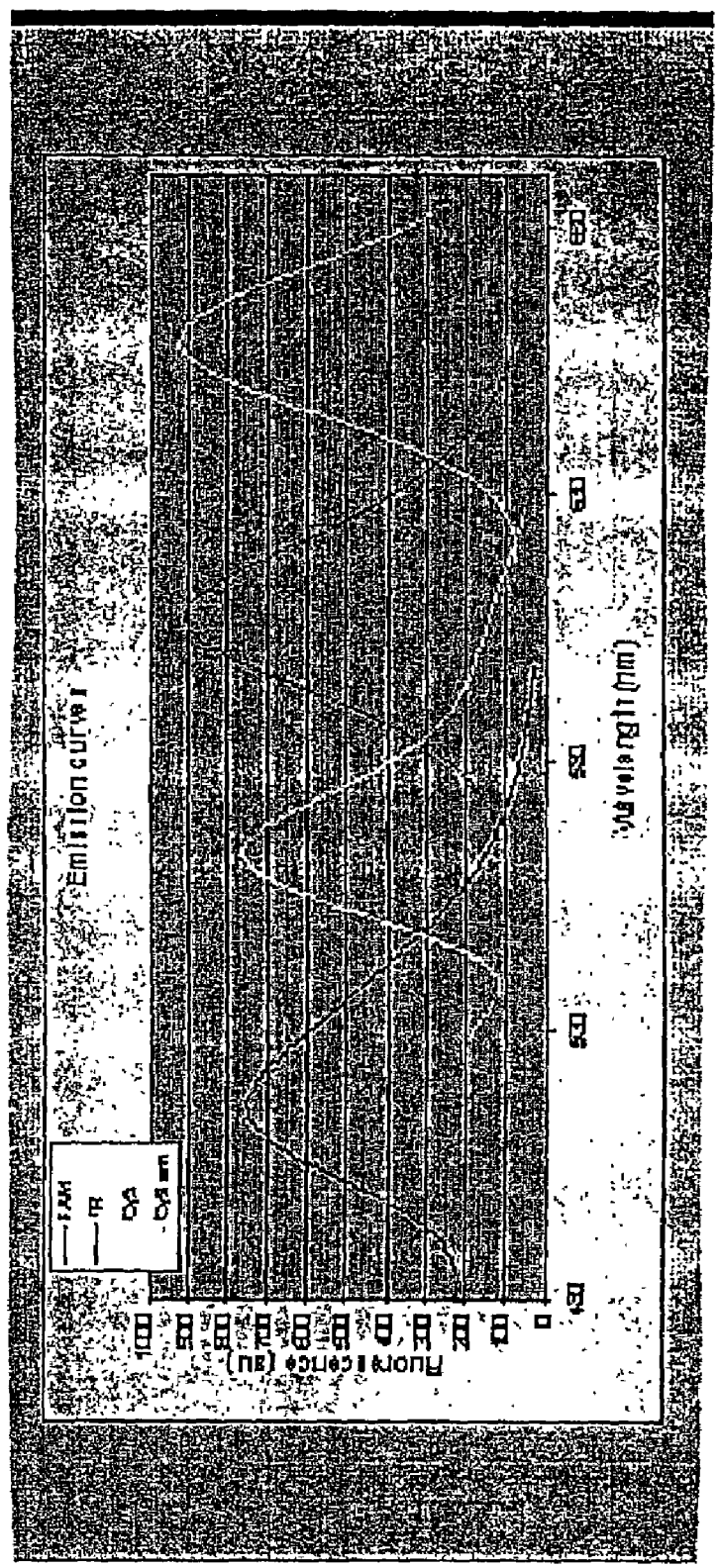
FIG. 4. Detection of up to 4 fluorescent signals in a single sample tube according to one aspect of the invention.
Figure 5:
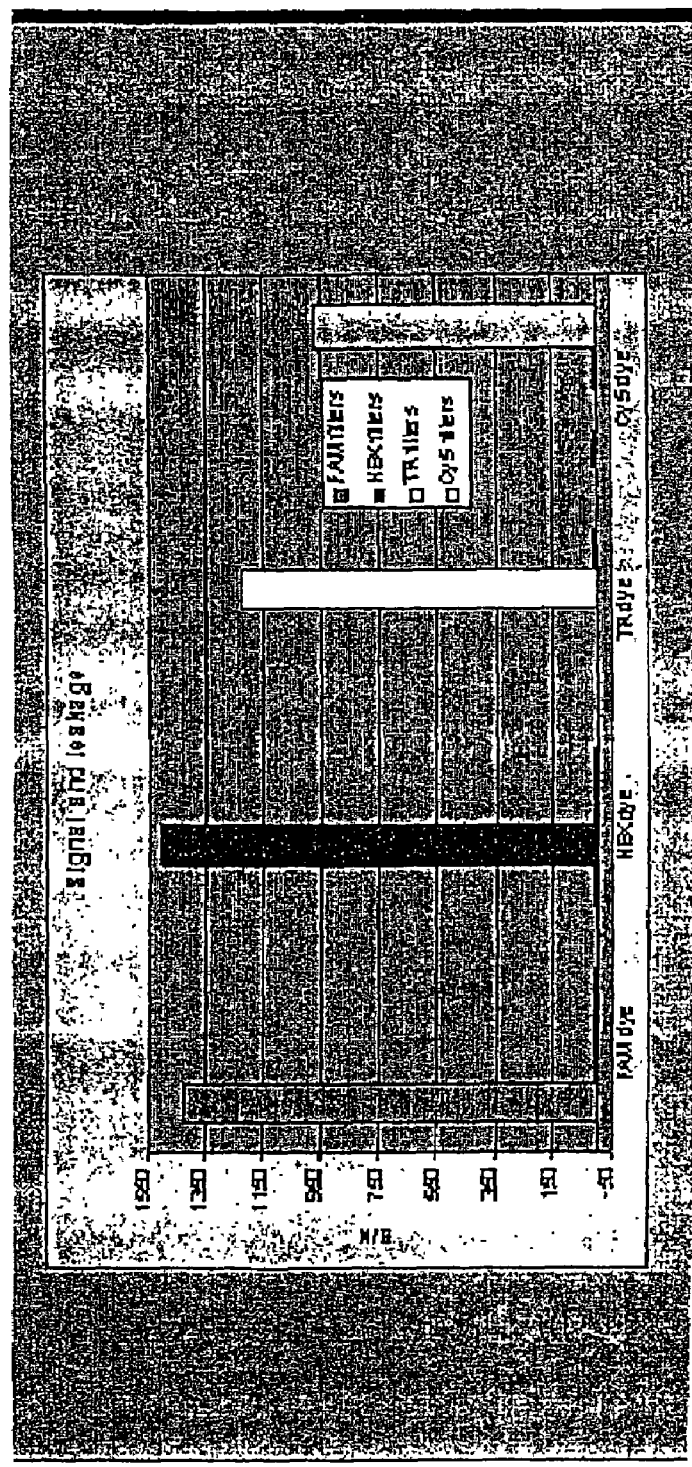
FIG. 5. Signal-to-noise ratios of various fluorescent dyes as measured by optimized filter sets according to one aspect of the invention.

The invention relates to algorithms for calculating an adaptive baseline of a PCR reaction, computer program products comprising the same, systems implementing the algorithms and methods for using the same. The algorithm calculates an adaptive baseline for data obtained from one or more labels evaluated in an amplification reaction. In one aspect, the method measures an actual signal obtained during a PCR cycle and generates a first plot for each one or more labels, determines a starting cycle and an ending cycle for one or more labels and calculates an adaptive baseline for each sample or label. The adaptive baseline can be subtracted from the actual signal observed during a PCR amplification cycle and used to calculate the amount of a nucleic acid template in a PCR reaction.

Definitions

The following definitions are provided for specific terms which are used in the following written description.

A "nucleic acid" is a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. "Nucleic acid" includes, without limitation, single- and double-stranded nucleic acid. The term "nucleic acid" as it is employed herein embraces chemically, enzymatically or metabolically modified forms of nucleic acid.

As used herein, the term "real time target template synthesis" or "real time synthesis" refers to a synthetic process during which a synthesized product can be analyzed as it is being generated without affecting subsequent synthesis of the product.

As used herein, "polymerase chain reaction" or "PCR" refers to an in vitro method for amplifying a target template sequence. A PCR reaction involves a repetitive series of temperature cycles and is typically performed in a volume of 50-100 μl. The reaction mix comprises dNTPs (each of the four deoxynucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule.

As used herein, the term "cycle" refers to a series of temperature steps over selected time periods. In one aspect, a cycle comprises three steps comprising: a step for denaturing a nucleic acid, a step for annealing a primer to a nucleic acid and a step for extending an annealed primer. A "step" refers to a time period of uniform temperature (within +/−1° C.). However, a sample well which is "cycled" through a PCR cycle does not necessarily have nucleic acids which can be denatured, annealed to primer, etc.; for example, the well can contain only buffer or only nucleotides and/or various other components of a PCR reaction mixture. A sample well is said to be cycled so long as it is exposed to the same temperatures for the same amounts of time which are suitable for denaturing, annealing, and extension. In one aspect, a PCR reaction comprises a plurality of cycles each cycle comprising a step of 90-100° C. (preferably, 94° C.) for 30 seconds-1 minute (preferably, 30 seconds), an annealing step from 37° C.-60° C. (preferably, 55-57° C. for 1-2 minutes (preferably 1 minute), followed by an extension step of 70-75° C. for 30 seconds to 1 minute (preferably, for 30 seconds).

As used herein, an "ending cycle" refers to a cycle before the amplification of a target template becomes detectable during a quantitative PCR reaction ("QPCR"). An "ending cycle" may be determined for a label(s) used for detecting the amplification of a target template in a sample.

As used herein, a "starting cycle" refers to a cycle after the initial variability of amplification subsides but before an ending cycle. In one aspect, the starting cycle is selected from the group consisting of: a first cycle which shows a different slope trend from its previous cycle; a cycle having a positive slope which is greater than the slope of its previous cycle; and a cycle having a slope less than 10% of an initial slope.

As used herein, the "detectable" means that an algorithm has determined the signal at a cycle has exceeded the background, i.e., there is a positive increase (e.g., at least 10%, 20%, 30% 40% 50% or more, or 2-fold, 3-fold, 4-fold or more increase) of determined signals for a given sample (e.g., by a given label in the sample) over the background level of signals.

As used herein, "background signal" refers to a signal before the ending cycle or a signal generated in a control sample comprising no template.

As used herein, the term "positive increase" is used to distinguish an ending cycle from a cycle where background signals fluctuate. A "positive increase" of signals reflects the increase of amplified product in a sample, e.g., as indicated by a signal generated from a label, rather than random background noise fluctuation. Typically, when there is a positive increase, there is a continuous increase of a fluorescent signal over at least 2 (or 3, or 4, or more) consecutive cycles.

As used herein, the term "Cycle X" refers to the cycle number at which the signal generated from a QPCR reaction first rises above a "threshold", i.e., where there is the first reliable detection of amplification of a target nucleic acid sequence. "Reliable" means that the signal reflects a detectable level of amplified product during QPCR. Cycle X generally correlates with starting quantity of an unknown amount of a target nucleic acid, e.g., lower amounts of target result in later Cycle Xs.

As used herein, the term "variability" refers to the change in the quality or quantity of the amplified PCR product which is not directly related to the amount of target nucleic acid in a sample. Variability may be due to inconsistencies in sample handling and the use of different reaction vessels, e.g., tubes, which cause the raw signal to vary from tube to tube (e.g., "tube-to-tube variability"). Variability, according to the invention, may be also due to instrument drift, which causes the raw signal from each individual sample to vary over time (e.g., "cycle-to-cycle variability"), regardless of the presence of the signal generated from the amplified nucleic acid product. Both types of variabilities reduce the precision of measurements of Cycle X.

As used herein, "cycle-to-cycle variability" is variability in amplification or synthesis between any two or more cycles of a real-time synthesis.

The term "growth curve" means a set of measurements of amplified nucleic acid product (e.g., dsDNA) present at or near the end of the extension portion of each cycle in a PCR reaction.

As used herein, an "actual signal", is a detectable signal generated by a label, where the signal can be directly measured by a signal detector. Preferably, the detectable signal is an optical signal (e.g., fluorescent label or chemiluminescent label) and the signal detector is an optical signal detector.

As used herein, a "label" is a molecule which generates a detectable signal, for example, an optical signal. Useful label types according to the invention include, but are not limited to, fluorescent, chemiluminescent, colorimetric, or enzyme labels.

As used herein, a "labeled probe" refers to a molecule which can be incorporated into or which can bind to an amplification product either directly or indirectly. For example, a labeled probe can be a labeled nucleotide which is incorporated into an amplification product or a labeled primer or a labeled probe can be a labeled molecule which binds to the amplification product itself (e.g., such as a probe to an internal sequence within an amplification product).

As used herein, the term "fluorescent" refers to the property of a molecule whereby, upon irradiation with light of a given wavelength or wavelengths, the molecule becomes excited and emits light of a longer wavelength or wavelengths.

The term "fluorophore" as used herein refers to a fluorescent molecule. There are a number of parameters which together describe the fluorescence characteristics of a fluorophore. These include, for example, the maximum wavelengths of excitation and emission, the breadth of the peaks for excitation and emission, the difference between the excitation and emission maxima (the "Stokes shift"), fluorescence intensity, quantum yield, and extinction coefficient. For biological or biochemical applications, longer Stokes shifts are generally preferred to shorter ones.

A "target template", according to the invention, refers to a template whose identity (e.g., sequence) or amount is to be determined in a test sample. A "target template" may be a region of a polynucleotide template that is to be replicated, amplified, and/or detected. In one embodiment, the "target template" resides between two primer sequences used for PCR amplification. A "target template" may also be an amplified product generated in a PCR reaction. A test sample, however, may contain more then one target template whose identity or amount needs to be determined, and each such target template may be a target template at the time when it is analyzed. According to the invention, when a plurality (n) of target templates present in a sample, there may be a plurality (n) of labels, each of which specifically binds to a specific target template and which is thus referred to as a "matched label" for the specific target template.

As used herein, "detecting a target template" refers to determining the presence of a given target polynucleotide sequence in a sample.

As used herein, "measuring a target template" refers to determining the amount of a given target polynucleotide sequence in a sample. The amount of a target polynucleotide sequence that can be measured or detected is preferably about 1 molecule to $10^{20}$ molecules, more preferably about 100 molecules to $10^{17}$ molecules, and most preferably about 1000 molecules to $10^{14}$ molecules or greater.

As used herein, an "oligonucleotide primer" refers to a single stranded DNA or RNA molecule that is hybridizable to a polynucleotide template and primes synthesis (e.g., such as enzymatic synthesis) of a second polynucleotide strand. Oligonucleotide primers useful according to the invention are between about 6-100, preferably, 10 to 100 nucleotides in length, more preferably about 17-50 nucleotides in length and most preferably about 17-45 nucleotides in length.

A "standard plot" refers to a plot generated by plotting an intensity of an optical signal (e.g., fluorescent intensity) as a function of known amount of a target template. A "standard plot" serves as a basis for quantifying an unknown amount of the target template in a sample.

As used herein, a "sample" or a "test sample" refers to any substance comprising a target template of interest (e.g., a target polynucleotide or a target polypeptide). The term "sample" thus can include a sample of polynucleotide (genomic DNA, cDNA, RNA) and/or polypeptide such as can be found in a cell, tissue, bodily fluid (including, but not limited to, plasma; serum; spinal fluid; lymph fluid; synovial fluid; urine; tears; stool; external secretions of the skin, respiratory, intestinal and genitourinary tracts; saliva; and blood), tumor, organ, organism (e.g., such as a microorganism), samples of in vitro cell culture constituents, an environmental sample (e.g., lake, reservoir, soil sample, and the like), or industrial sample (e.g., a commercial food product, an industrial waste product, and the like).

Overview of the PCR Procedure

Fundamental to the system of the invention is the use of a novel adaptive baseline subtraction algorithm which determines the starting and ending cycles prior to amplification based on the characteristics of each sample being evaluated in an amplification reaction, such as during real-time QPCR. The algorithm calculates a baseline from endpoints independently determined for each sample unlike prior art methods which calculate a baseline based on the endpoints for all samples. The adaptive baseline algorithm according to the invention can be used to provide a more accurate and/or precise measure of the threshold cycle which reflects a first reliable detection of the amplification product ("Cycle X").

The algorithm can be used in the analysis of different types of amplification schemes in addition to PCR. Generally, the algorithm is used to evaluate amplification schemes which require the use of a nucleic acid polymerase in an amplification reaction during which a population of amplified nucleic acid product (e.g., dsDNA) increases. Exemplary amplification schemes include, but are not limited to, PCR; ligase-based amplification schemes, such as ligase chain reaction (LCR); Q-beta replicase-based amplification schemes; strand displacement amplification (SDA) schemes (such as described by Walker et al, Nucleic Acids Research, 20:1691-1696 (1992)), and the like. A comprehensive description of nucleic acid amplification schemes is provided by Keller and Manak, In *DNA Probes*, Second Edition (Stockton Press, New York, 1993).

Generally, the algorithm is used to calculate a baseline for amplification reactions monitored by including a label in the reaction mixture. The label can interact with an amplified product (e.g., by being incorporated into the amplified product or binding to the amplified product) to generate a detectable signal, for example, an optical signal, whose measure can be correlated with the amount of amplified product in the reaction. Useful label types according to the invention include, but are not limited to, fluorescent, chemiluminescent, colorimetric, or enzyme labels.

Examples of useful fluorescent labels include fluorescein, rhodamine, phycoerythrin, phycocyanin, allophycocyanin, and fluorescamine. Examples of useful chemiluminescent label types include luminal, isoluminal, aromatic acridinium ester, imidazole, acridinium salt, oxalate ester, luciferin, luciferase, and aequorin. Examples of useful enzyme labels include malate hydrogenase, staphylococcal dehydrogenase, delta-5-steroid isomerase, alcohol dehydrogenase, alpha-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, and glucoamylase, acetylcholinesterase.

Suitable labels can be coupled to (e.g., covalently bonded), or incorporated into polynucleotides, polypeptides, antibodies or antibody fragments through standard techniques known to those of ordinary skill in the art. See, for example, Kennedy et al., Clin. Chim. Acta 70:1-31 (1976); and Schurs et al., Clin. Chim. Acta 81:1-40 (1977).

In one embodiment of the invention, a fluorescent labeled molecule is used for monitoring amplification of a product during PCR. The fluorescent labeled molecule, when interacting with, or incorporated into, an amplified product generated by an amplification reaction (e.g., a PCR reaction), emits a detectable signal when appropriately excited (e.g., during at least the extension portion of each cycle of a PCR reaction). The amplification reaction is performed for a sufficient time (e.g., thermal cycling the reaction mixture for a sufficient number of cycles during a PCR reaction), to establish a desired final concentration of an amplified nucleic acid product.

The raw signal (e.g., fluorescent intensity) observed at any point in an amplification reaction is offset using the algorithm according to the invention to remove background signal unique for a particular sample in which the signal is observed. The resulting signal provides a truer measure of the target molecule being amplified in the sample. In one aspect, the background signal or baseline is determined as the expected signal in a tube or well comprising the sample in the absence of a target nucleic acid. In contrast to prior art methods, in which a single baseline is determined for all samples being evaluated, the instant invention uses the algorithm to determine a baseline which is specific for each individual sample whose amplification is being monitored.

In one aspect, the algorithm is implemented during a QPCR reaction. A typical process of QPCR involves amplifying a target template in the presence of at least one label which emits signals corresponding to the amounts of amplified product during QPCR; collecting the signals emitted, and storing the collected signals in a processor. The collected signals are analyzed and subsequently displayed on the screen of a user device in communication with the processor.

In one embodiment, the method of the invention for implementing the algorithm comprises the steps of: detecting and measuring the intensity of signal in a sample during at least the extension portion of each of a plurality of starting cycles is chosen (cycles before amplification has occurred in any tube), converting the intensity to molar concentration values of an amplified product (e.g., dsDNA), storing in a processor the molar concentration values for each of the extension portions of each of the cycles; and generating a measured curve representing the molar concentration of the amplified product (e.g., dsDNA) as a function of cycle number based on the stored concentration values.

Conversion of signal intensity measurements to molar concentrations can be performed by methods routine in the art. For example, PCR samples can be replaced with standard solutions (e.g., photometric standards) of DNA containing all the same reaction materials in the same amounts, except with several known molar concentrations of the nucleic acid template ranging from none (e.g., baselines) through the range of concentrations likely to be produced by a PCR reaction for detecting the unknown amount of the target nucleic acid in a sample. Then, by subtracting the baseline signals from the signals measured on these known photometric standards, a working curve is generated relating measured signal corrected for baseline background with the concentration of standard template dsDNA. Baseline subtraction can be performed prior to, or after, the conversion of signal intensity measurements to molar concentrations. In one embodiment, baseline subtraction is performed before converting signal intensity measurements to molar concentrations. In another embodiment, baseline subtraction is preformed after signal intensities are converted to molar concentrations. It is not necessary to perform PCR to prepare this working curve. Standard solutions with known molar concentrations of DNA may be used.

In a preferred embodiment, the measured curve was generated representing the signal intensity of the amplified product (e.g., dsDNA) as a function of cycle number based on the stored concentration values, without converting the intensity to molar concentration values.

In one aspect, the starting molar concentration of target nucleic acid in a sample comprising unknown amounts of nucleic acids is determined by obtaining aliquots of the test sample and performing the same amplification reactions on the aliquots under the same conditions that were used for standard samples comprising known amounts of target nucleic acids. A growth curve is recorded for each of the aliquots by obtaining a set of measurements of amplified nucleic acid product (e.g., dsDNA) present at or near the end of the extension portion of each cycle in the amplification reaction and measurements are converted to molar concentrations of amplified product. The best fit between a growth curve of one of the aliquots and the working curve for a standard is calculated, e.g., such as by a single-variable successive approximation method. The concentration of the standard whose working curve provides the best fit with the growth curve of the aliquot of the sample comprising unknown amounts of nucleic acids is taken as the concentration of the aliquot of the unknown sample. Baseline subtraction is also applied to the measured signals generated for the sample containing an unknown amount of target nucleic acid, prior to, or after, the conversion of signal intensity measurements to molar concentrations and is described more specificity below.

Method Employing the Adaptive Baseline Algorithm

During real-time PCR, actual signals or raw data for each given sample well of a multiple sample well holder inserted into a real-time PCR system (such as Stratagene®'s Mx400 thermocycler) are detected at every cycle of the PCR amplification reaction. One or more wells may serve as control wells by comprising all reagents used for the PCR amplification except for a nucleic acid template. The actual signals generated in each cycle from one or more labels in one or more sample wells can be collected into a data set. The data set may comprise the average (i.e., arithmetic mean) signal of each of the one or more labels, or minimum or maximum signals generated from label(s) for each cycle.

A conventional PCR baseline subtraction algorithm assigns the same starting and ending cycles for all the wells in a PCR reaction. However, it is unavoidable that PCR amplifications may vary from cycle to cycle and from sample to well. So for some wells, the ending cycle may be too big. In this case, the amplification plot will start with a high negative slope, show amplification later than it should, and droop significantly over the later cycles during the amplification (see, as shown in FIG. 1). For some other wells, the ending cycle may be too small, such as where the amplification plot will start with a high positive slope and show amplification earlier than it should (see FIG. 1). If the ending sample is too small, the initial slope is not affected much, but the measured amplification, specifically and most importantly Cycle X, is much less precise.

In the present invention, the starting and ending cycle are determined individually and uniquely for each sample well and/or each dye being evaluated. For each sample well and/or dye, a first plot is generated by plotting the actual signals generated by a label in the sample well as function of cycle number. In a preferred embodiment, a second plot is generated which plots a 3-point moving average ("MA") of the actual signals as a function of cycle number, obtaining a series of averages from every 3 cycles as a function of cycle numbers. A method for calculating a 3-point MA is shown in Table 1.

TABLE 1

Calculating 3-point MA*

| Cycle | 1 | 2 | 3 | 4 | 5 | 6 |
|---|---|---|---|---|---|---|
| Signal value | $A_1$ | $A_2$ | $A_3$ | $A_4$ | $A_5$ | $A_6$ |
| 3-point MA | | | $MA_1 = (A_1 + A_2 + A_3)/3$ | $MA_2 = (A_2 + A_3 + A_4)/3$ | $MA_3 = (A_3 + A_4 + A_5)/3$ | $MA_4 = (A_4 + A_5 + A_6)/3$ |

*The number of cycles can be extended to the actual number of cycles in a PCR reaction.

The 3-point MA calculated may be used for determining end points for the adaptive baseline (e.g., the starting and the ending cycles before real amplification occurs in an individual well being evaluated) and is calculated for each data set, i.e., for each sample well.

In a preferred embodiment, the starting cycle (a cycle after the initial variability of an amplification reaction has abated but before detectable amplification starts) is assigned as one of the following: 1) a first cycle which shows a different slope trend from its previous cycle, e.g., becoming positive where a previous slope was negative, or becoming negative where a previous slope was positive; 2) a cycle having a positive slope which is greater than the slope of its previous cycle; and 3) a cycle having a slope less than 10% of an initial slope which is the first slope of the first or the second plot. If no cycle satisfies the criteria in 1), 2) and 3), the starting cycle is assigned as cycle 0.

In another preferred embodiment, the starting cycle is limited to be a cycle between the first and the eighth cycle. This limitation may decrease the spread of the data and/or reduce the incidence of artificially spurious results.

In another embodiment, the algorithm is based on the noise level in the data rather than on the first and second derivatives. In this case, the algorithm calculates the standard deviation of the points around a proposed baseline. It then compares the points up to cycle six against this value. If all the points before cycle six are outside this value, then cycle seven is the starting cycle. If not, the algorithm looks at the points up to cycle five. The algorithm continues until the condition is met but cycle 1 is not analyzed by the algorithm.

In order to determine the ending cycle for an individual sample being evaluated, it is critical to determine Cycle X. Cycle X refers to a cycle where reliable detection of amplification starts. Cycle X may be identified as a cycle which has a maximum change of slope from its previous cycle and has four immediately subsequent cycles, each of which has an increased slope compared to its previous cycle. The steps for determining Cycle X may comprise sorting points on a plot of fluorescent intensity vs. cycle number and identifying a first and second derivative at different points on the plot. The first derivative represents a slope corresponding to the change in fluorescent intensity observed from one cycle to the next cycle. The second derivative the change during the amplification reaction.

For any point representing a cycle, if the first derivative is positive and the next four points have an increasing slope, the cycle is accepted as Cycle X. If this criteria is not met, the cycle is rejected and the next point corresponding to a cycle is evaluated to determine whether the cycle fits the criteria for Cycle X.

In one embodiment, Cycle X is determined by evaluating points which represent the first 8 cycles of the PCR reaction. If a Cycle X is accepted within the first 8 cycles, then an ending cycle (a cycle which occurs before the amplification of a target template) is assigned by subtracting a certain arbitrary number of cycles from Cycle X. The certain number to be subtracted may vary from experiment to experiment and can be decided according to how well the adaptive baseline fits for a sample being evaluated, as described further below. In a preferred embodiment, the ending cycle is three, or two, or one cycle before Cycle X.

In another embodiment, Cycle X is not determined to be within the first 8 cycles of the PCR reaction. In this embodiment, Cycle X itself is assigned as the ending cycle.

In another embodiment, Cycle X is determined based on the maximum second derivative of an amplification curve. Cycle X is set as a fixed fraction of the signal at the maximum second derivative. In yet another embodiment, Cycle X is determined based on two signal levels, for example, the maximum second derivative and the maximum slope, or the maximum second derivative and the minimum second derivative. In still another embodiment, Cycle X is determined based on the ending cycle determined by the adaptive baseline.

In one embodiment, Cycle X is determined based on the range of Cycle Xs for groups of replicate samples—samples prepared identically and identified to the instrument as being replicates. Because these samples are the same, they should produce the same threshold cycle. In this case, Cycle X is determined as the cycle where the signal level at which the spread of threshold cycles for all replicates is minimized.

If the ending cycle were selected more accurately, the range for which the data are off-scale would be much smaller. The adaptive baseline algorithm that determines the ending cycle is based on the maximum change in slope (second derivative) of the amplification curve. In one embodiment, the algorithm subtracts three cycles to generate the ending cycle. In another embodiment, the algorithm calculates the ending cycle by subtracting four cycles instead of three cycles. Various checks can be applied to eliminate spurious endpoints—when, for example, noise, rather than signal, creates largest second derivative. In one embodiment, the ending cycle on the cycle with the maximum second derivative was performed by checking on the sign of the first derivative and the trends of the first and second derivatives around that cycle.

The starting and ending cycle determined for an individual well may be further adjusted so that the baseline more accurately adjusts for the variability of the PCR reaction due to instrument drift and/or sampling inconsistencies. In one embodiment, a calculated growth curve is generated for a template. This growth curve reflects the signal generated in each cycle with known amounts of the template. The starting and ending cycle may be decided for a PCR amplification reaction as above, with known or unknown amount of a template. The actual signals of amplification are measured. A measured growth curve may be generated from the actual signals using an adaptive baseline derived based on the starting and ending cycles determined as described above. The measured growth curve is then compared to the calculated growth curve so that the starting and ending cycles for a sample can be adjusted according to the quality of fit between measured and calculated growth curves.

The quality of the fit between measured and calculated growth curves may be measured by how small the average of the squares of the differences can be made. A useful measure is the root mean square error of fit, or "rmse". The rmse is calculated by squaring the difference between the measured signal intensity and the predicted (e.g., calculated) value at each cycle. The average of these squares over the range of the fit (e.g., the number of cycles included in the fit) is calculated, and the square root is determined to yield the rmse for the fit.

In one aspect, the rmse is determined according to the formula:

$$rmse = \sqrt{\frac{\sum_{i=S}^{E}(m \times i + b) - y_i}{N}} \qquad (1)$$

where N is the number of cycles between the starting and the ending cycles; S is the starting cycle; E is the ending cycle; $y_i$ is a signal of an $i^{th}$ cycle; and m and b are parameters of the best fit line.

The rmse increases rapidly once the signal begins to amplify above the background. In one aspect, the ending cycle is varied to plot rmse of fits against cycles fit through. The ending cycle at which the rmse exceeds a specified value is chosen. It will be obvious to one skilled in the art that any method that gives equivalent results will work. For example, any statistical method routinely used in the art to determine the significance of observed differences can be used.

Another method of determining the ending cycle for each amplification reaction is to plot rsq of the least mean square fit of the baseline function to the data as a function of cycle fit through. The ending cycle could be defined as that cycle at which the rsq value exceeds a specified value.

The measured and calculated growth curves may be compared in their polynomial or logarithmic forms or in other suitable forms.

Another way of adjusting the starting and ending cycles for a sample is to assign an ending cycle arbitrarily. In one embodiment, if the relative distance between the start and ending cycles is 0, e.g., when the start and the ending cycles are at the same cycle), then the ending cycle is arbitrarily assigned to the last cycle of the amplification reaction. The starting cycle is arbitrarily assigned at cycle 0.

In another embodiment, if the relative distance between the start and ending cycles is greater than 0 (i.e., when the start and the end cycles are not at the same cycle), but smaller than a certain number of cycles (e.g., 6-12 cycles), then the starting and ending cycles are arbitrarily assigned so that the distance between the starting and ending cycles is the certain number (e.g., 6, or 7, or 8, or 9, or 10, or 11, or 12).

In a preferred embodiment, the certain number is arbitrarily determined to be 8. For example, if the relative distance is less than 8 cycles, then the starting and the ending cycles are set apart by 8 cycles. This is done by adjusting the number of starting cycle relative to the number of ending cycle. Thus, if the ending cycle is at cycle 10, the initial starting cycle is at cycle 5, then the starting cycle is adjusted to cycle 2 so as to maintain a distance of 8 from the ending cycle. If the ending cycle is at a cycle less then or equal to 8, then the starting cycle is set to cycle 0 and the ending cycle is set to cycle 8 so to maintain a distance of 8 between the start and the ending cycle.

In another embodiment, prior to adjusting start and ending cycles based on their relative distance, the start and ending cycles are adjusted based on standard deviation error by comparing points representing fluorescent intensity at given cycles between the starting and ending cycles on a measured growth curve with points on a calculated growth curve. The starting and ending cycles could be adjusted inward (towards each other) until all points are within some standard deviation error of each other.

The number of cycles which should be run in practicing the method should be at least enough to raise the intensity of a fluorescent signal of an amplified product (e.g., dsDNA) in a sample to a value above the limit of which can be detected by the means used to measure the fluorescent intensity (e.g., the detector of a thermocycler) at the end of each cycle for a sample with the smallest starting concentrations of interest. Larger numbers of cycles than this will give better results, with decreasing benefit of added cycles once the molar concentration of amplified product has ceased to increase significantly in each cycle.

Apparatus Required for Applying the Invention to Quantitative Real-Time PCR

An apparatus useful for applying the algorithm and method of the invention may comprise a thermal cycler, an input device for collecting signals (e.g., a detection system), an analyzing device (e.g., a processor) for analyzing signals and an output device for displaying data obtained or generated by the analyzing device (e.g., a user device such as a computer in communication with the analyzing device). The analyzing device may be connected to a thermocycler through an input device as known in the art, and/or connected or contain an output device as known in the art for data display. In one embodiment, the analyzing device is a computer, for example, as shown in FIGS. 12A and 12B.

A thermal cycler used to perform the method may be of a conventional design which can hold up to 96 reaction samples in a thermal cycling block in standard PCR tubes or in wells of a PCR sample plate (collectively referred to as "a sample block comprising sample wells" herein). Where tubes are used, these preferably have transparent caps (e.g., comprise polypropylene or another transparent, heat-resistant plastic). Preferably, the lid of the thermocycler over the tubes/wells is particularly adapted to receive and support the input devices of a detection system.

In one aspect, the detection system is suitable for detecting optical signals from one or more fluorescent labels. Preferably, the system comprises and one or more scanning optical fibers for transmitting light to and receiving light from sample tubes within the assembly. Preferably, a plurality of optical fibers (e.g., one per different type of optical signal or label being detected) is used to scan the surface of the tubes (e.g., row by row) collecting a plurality of optical signals per scan (preferably at least 9 optical signals) which are averaged to generate an average signal per sample tube per scan. Preferably, the detector also comprises suitable signal amplification and conversion circuitry for converting light signals to a digital input to the processor which is in communication with the assembly. The detector also may comprise a digital camera system such as described in the Higuchi et al., 1993, *Biotechnology* 11(9): 1026-30.

The output of the detection system (e.g., signals corresponding to those generated during the amplification reaction) is fed to the processor for data storage and manipulation. In one embodiment, the system detects multiple different types of optical signals, such as multiple different types of fluorescent labels and has the capabilities of a microplate fluorescence reader (e.g., is able to isolate and analyze the intensity of signals obtained from individual wells).

The detection system is preferably a multiplexed fluorimeter containing an excitation light source, which may be a visible light laser or an ultraviolet lamp or a halogen lamp, a multiplexer device for distributing the excitation light to the individual reaction tubes through the fiber optics and connectors for receiving fluorescent light from the reaction tubes, a filtering means for separating the fluorescence light from the excitation light by their wavelengths, and a detection means for measuring the fluorescence light intensity.

Figure 6:
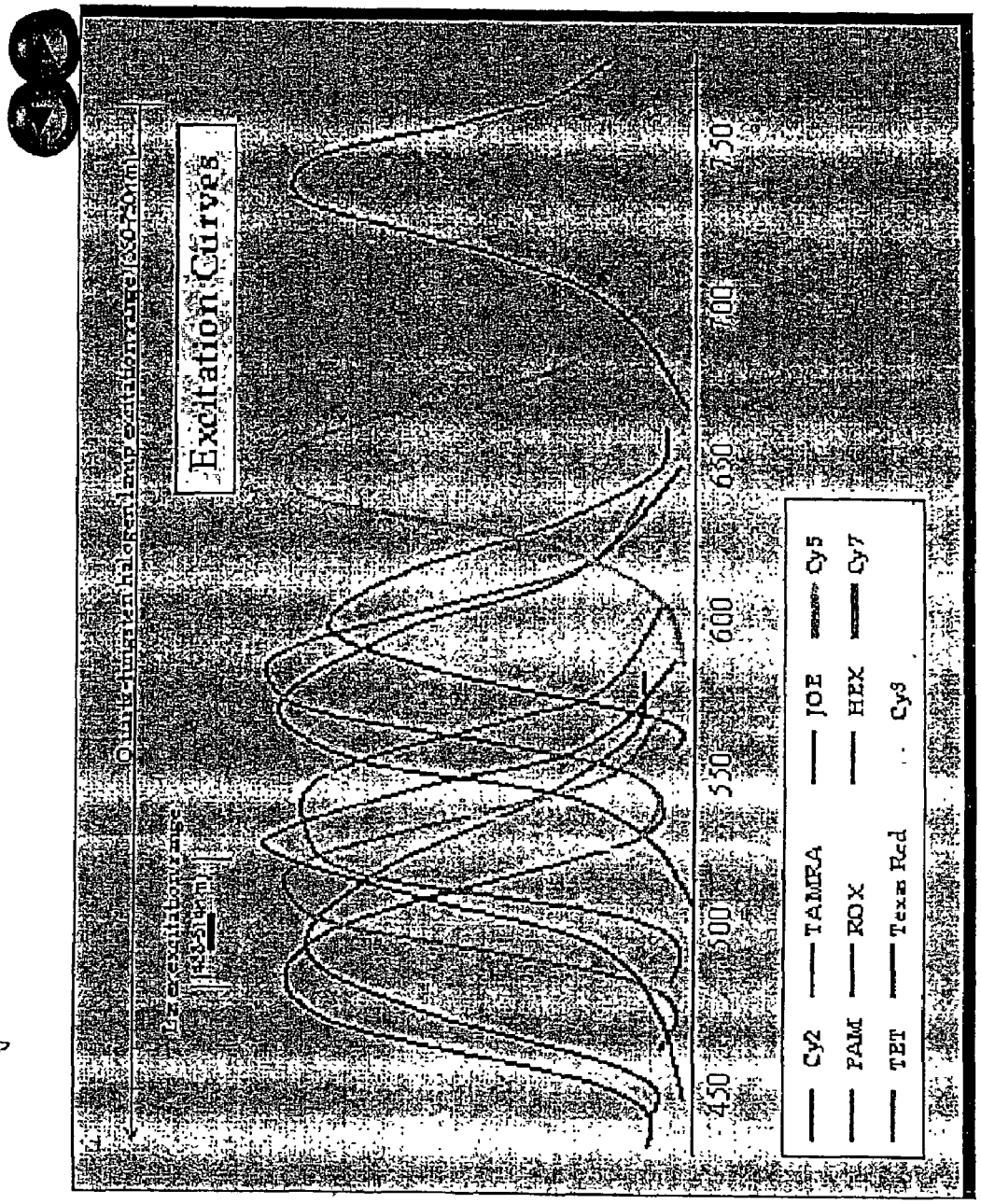
FIG. 6. Fluorescent dye emission curves for typical dyes used according to one aspect of the invention.
Figure 7:
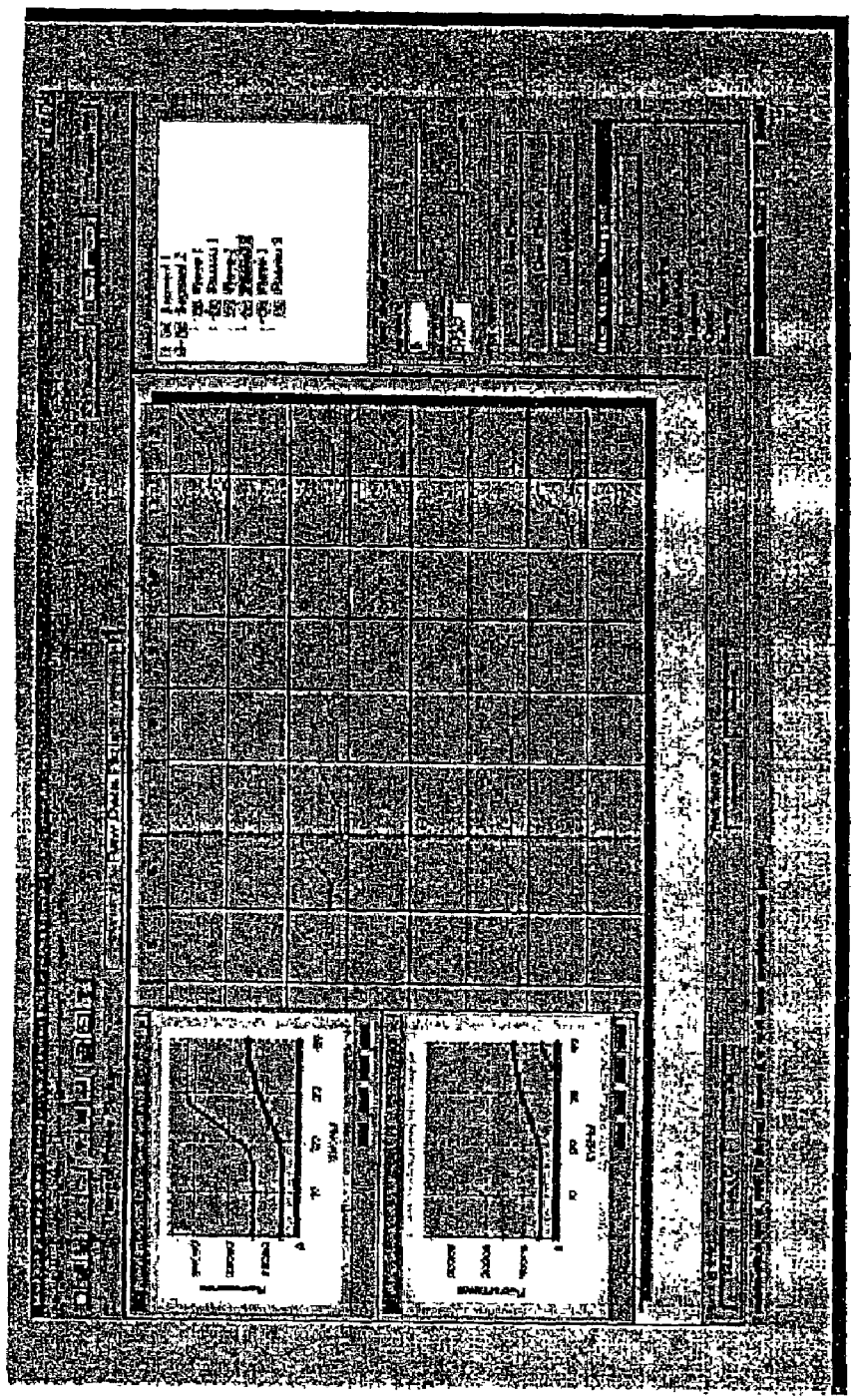
FIG. 7. Real-time amplification plots as PCR progresses shown as fluorescent signal as a function of cycle number according to one aspect of the invention.

Preferably, the detection system of the thermocycler provides a detection range of 350 nm to 830 nm, allowing greater flexibility of fluorophore choice, providing high sensitivity and excellent signal-to-noise ratio. The system's light source preferably generates an extended excitation range from 350 to 750 nm. This enables a user to choose fluorophores with little or no spectral overlap, producing clean, delineated signals for superior multiplexing. Optimized interference filters also can be provided to precisely match the excitation and emission wavelengths of each fluorophore whose intensity is being evaluated, to block out unwanted cross-talk from spectrally adjacent fluorophores (see, e.g., as shown in FIG. 6). For example, FAM, TET, HEX/JOE/VIC, TAMRA, Texas Red/ROX, Cy5 and Cy3 filter sets are available commercially and custom filter sets can be made for other fluorophores (Stratagene, Calif.).

Preferably, real-time amplification plots are viewed as amplification progresses. This enables a user of the assembly to determine at a glance how an experiment is running at any time during thermal cycling, rather than waiting until the end of the run. A user can choose to abort a run if a problem develops in a reaction, or stop the experiment and save the data as soon as the desired information is generated.

Optical signals received by the detection system (e.g., corresponding to fluorescent signal intensity at a given time point in a given tube) are generally converted into signals which can be operated on by the processor to provide data which can be viewed by a user on a display of a user device (e.g., a computer) in communication with the processor. Preferably, the program of the analyzing device allows robust communication between the thermocycler device and the user device such that even in the event of a power loss to the computer or communications error, data collection continues. When communication is restored, the data from the run is transferred from the thermocycler's embedded software to the software on the computer to ensure that the experiment may be completed and the data successfully saved.

Figure 8:
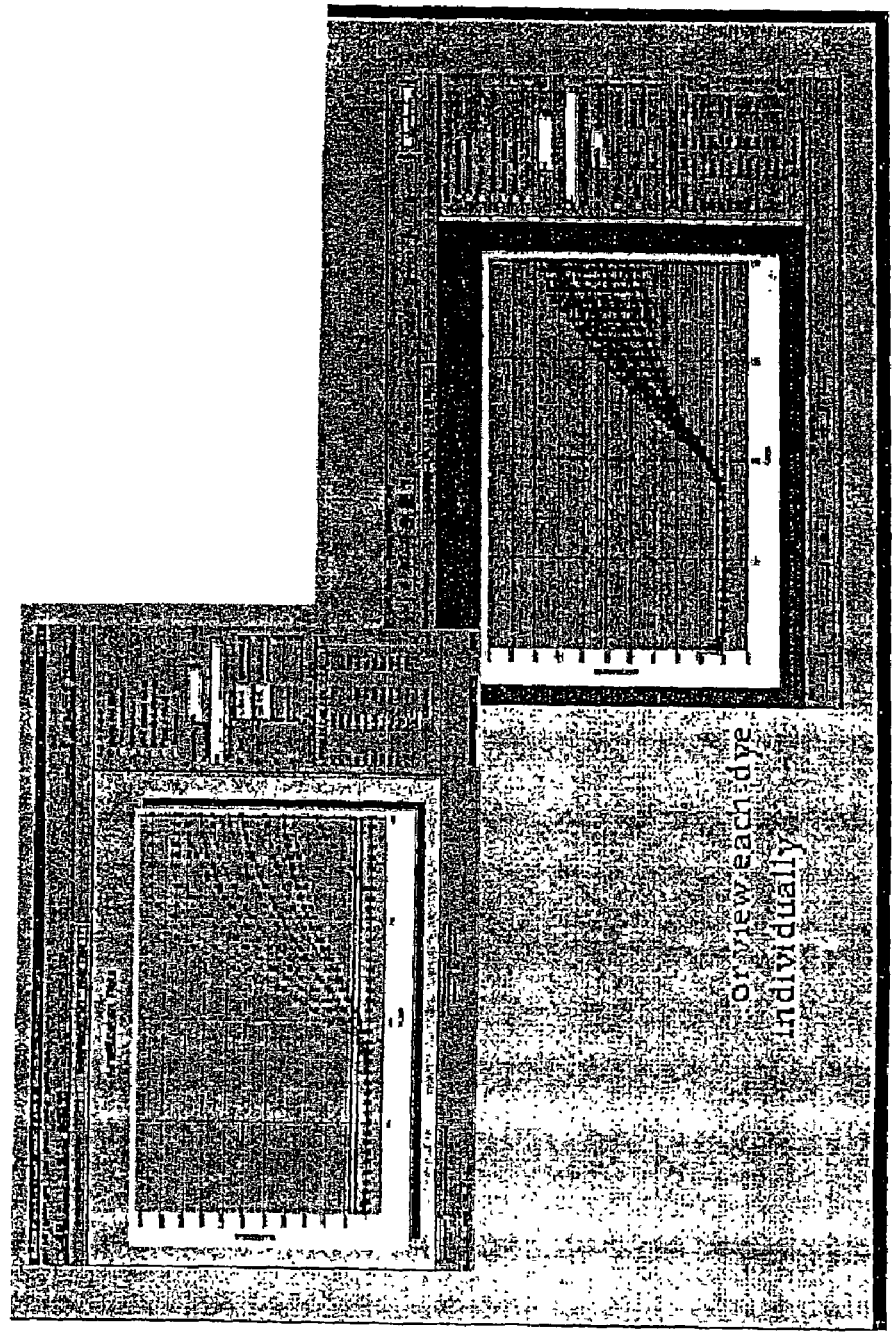
FIG. 8. Up to 4 fluorescent signals are viewed in a single amplification plot according to one aspect of the invention.
Figure 9:
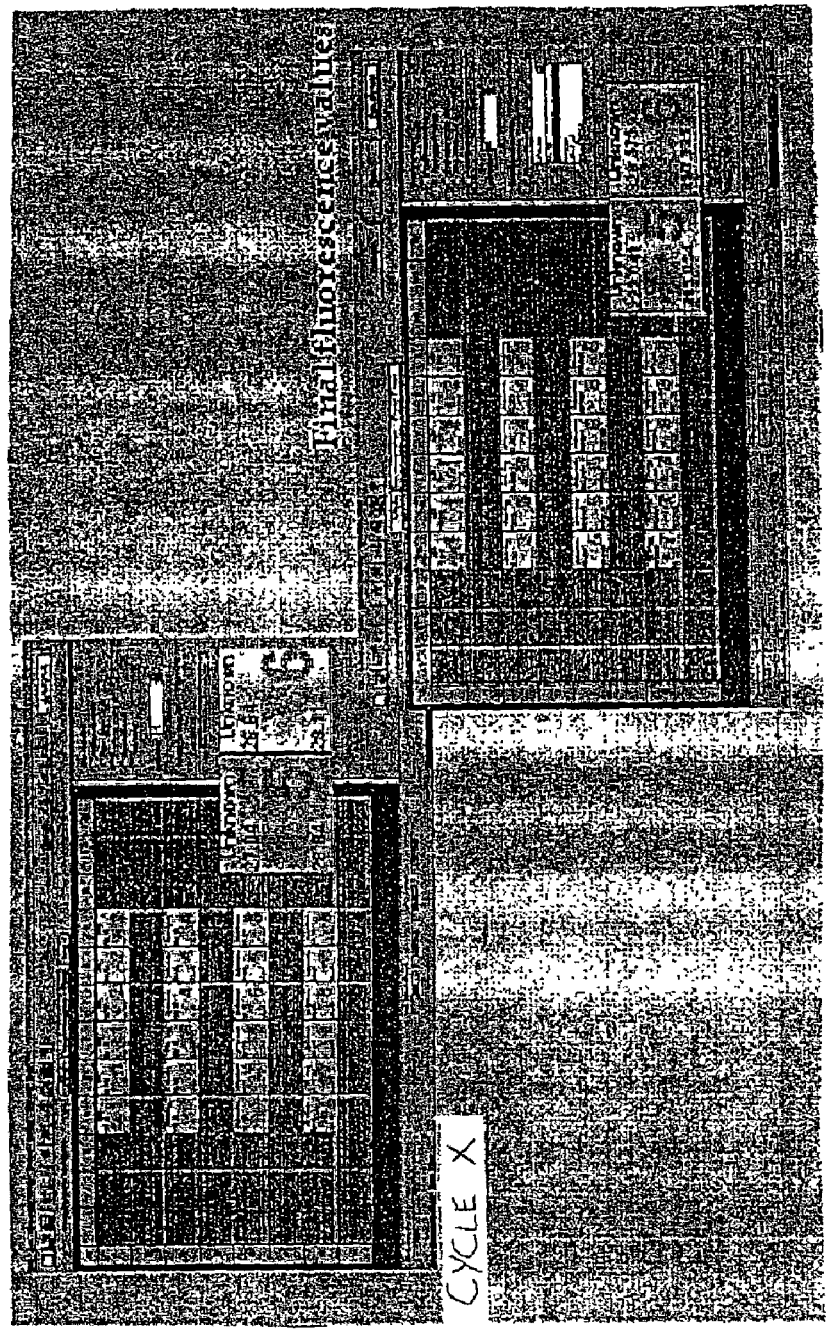
FIG. 9. Amplification plot shown generated using baseline subtraction according to one aspect of the invention.
Figure 10:
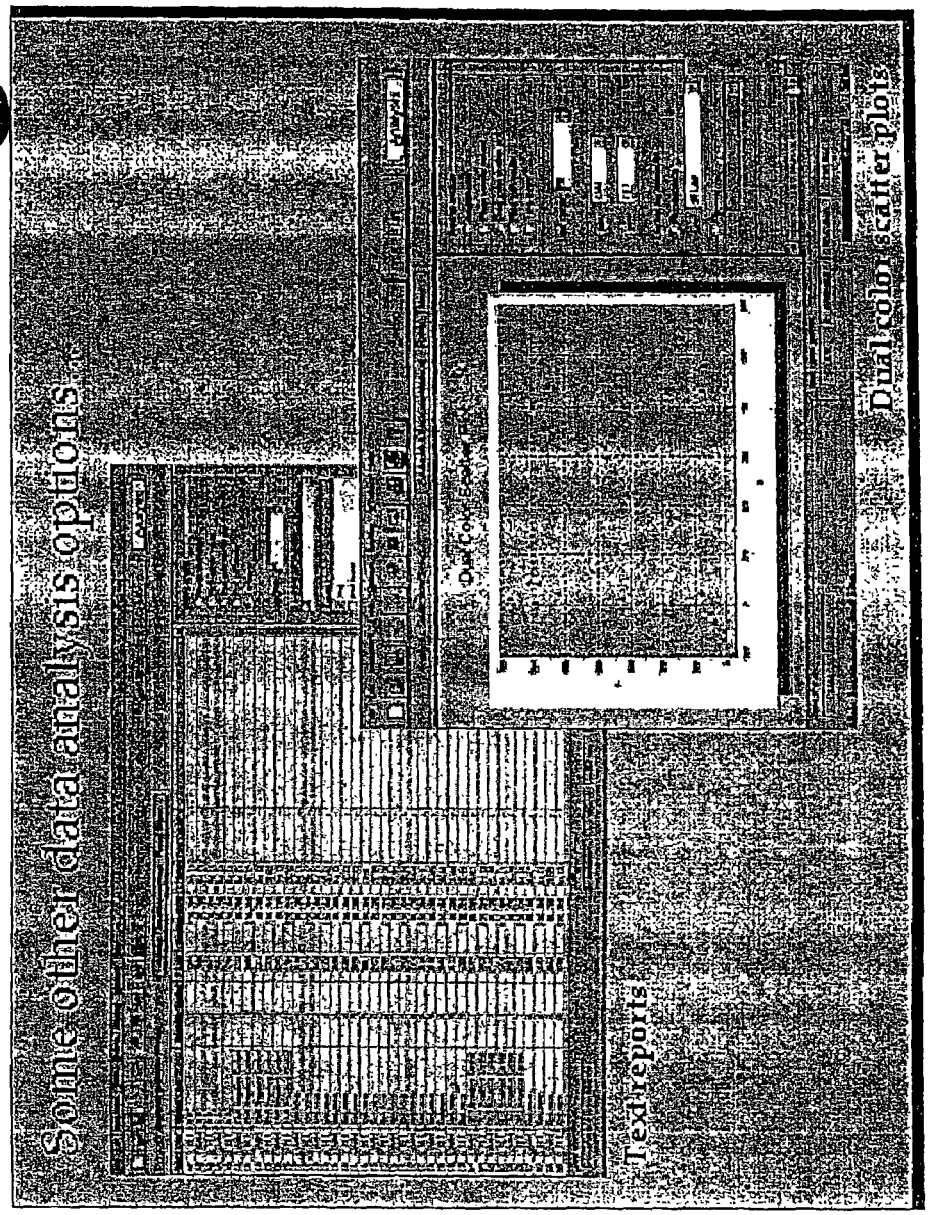
FIG. 10. Data analysis options provided on the interface of a user device in communication with a thermocycler used for QPCR and adapted for performing baseline subtraction according to one aspect of the invention.

The user device may comprise a user interface or may be a conventional commercially available personal computer (PC) system with a keyboard and video monitor. Examples of data which can be displayed by the user device include amplification plots (see, FIG. 8), scatter plots (see, FIG. 10), sample value screens for all the tubes in the assembly and for all labels used, an optical signal intensity screen (e.g., fluorescent signal intensity screen), final call results, melting curves, annealing ranges, text reports, and the like. In a preferred aspect, the user device can display working curves, growth curves, and first and second plots, and the results of various operations on these curves/plots. For example, in one aspect, the user device displays the rmse obtained after the analyzing device/processor determines the fit between a first and second plot.

The user device also can display a user interface to enable a user to provide instructions to the analyzing device or processor; for example, instructions to change the cycling parameters of the system or to implement baseline subtraction. In one aspect, in response to instructions from the user device, the analyzing device or processor implements a program which comprises the adaptive algorithm of the invention. The algorithm may be a part of a program product which may be used with a computer, e.g., as part of software used by the computer or as part of an application stored in the memory of the computer or in the memory of a server which the computer can access.

In one aspect, the analyzing device analyzes signals from sample tubes or wells in the sample block of the thermocycler detected by the detection system. The analyzing device determines a starting cycle and an ending cycle for tube or well in the sample block according to the method of the invention described above. In one embodiment, the analyzing device also adjusts the starting and ending cycles, e.g., by comparing a measured growth curve to a calculated growth curve. The starting and ending cycles are used in to determine an adaptive baseline, so each tube or well is assigned its own starting and ending cycles to avoid variabilities caused by instrument drifts and sampling inconsistencies. Comparison of a measured growth curve and a calculated growth curve for each tube/well is performed by a person using the computer (e.g., by implementing programs to determine a rmse) to adjust starting and ending cycles as a means of determining the baseline for each tube and well. A baseline unique for each tube/well is subtracted from the raw signal obtained during the amplification reaction, to obtain a measured signal which is a truer reflection of the amount of target sample in the tube/well.

EXAMPLES

Example 1

Figure 11A:
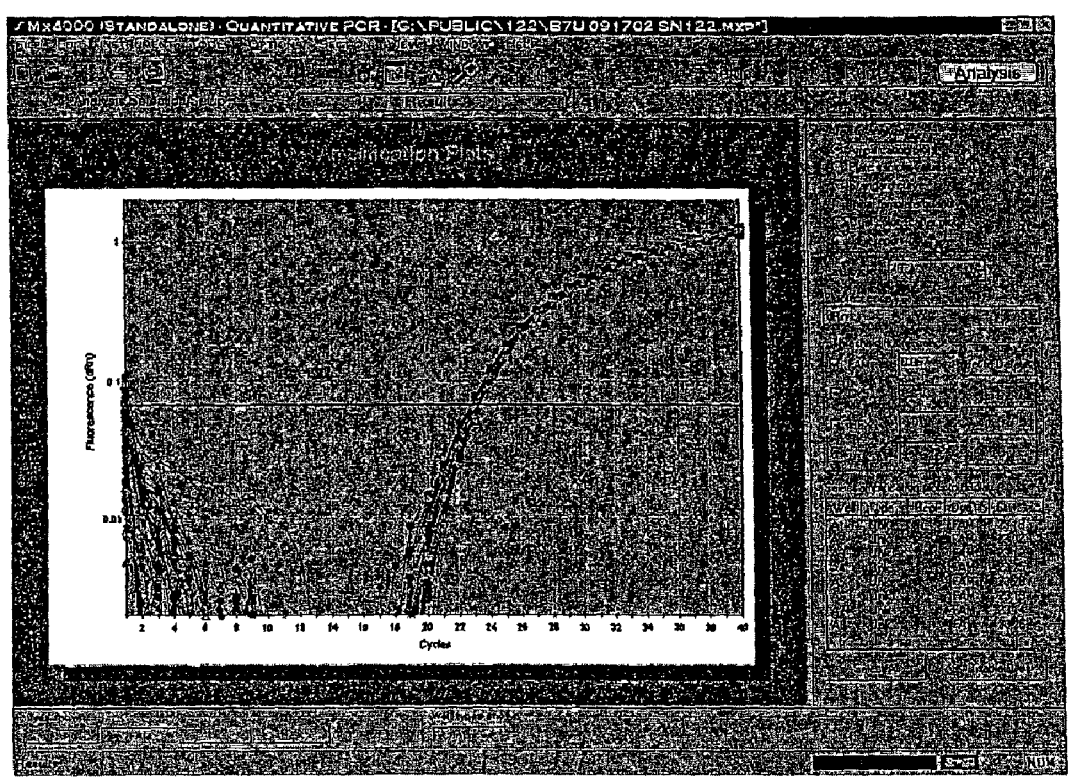
FIG. 11A is a graph showing the result of a PCR amplification analysis where the starting cycle is not limited to a cycle between 1 and 8 according to one embodiment of the invention.
Figure 11B:
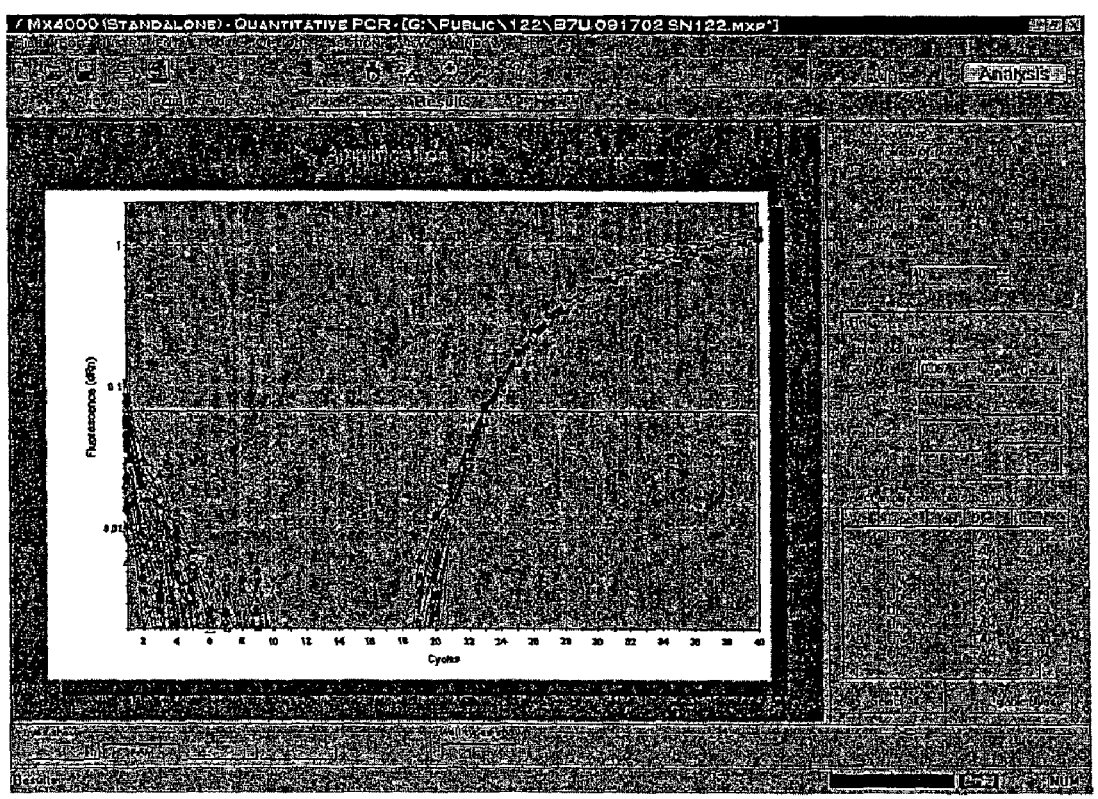
FIG. 11B is a graph showing the result of the same PCR amplification analysis where the starting cycle is limited to a cycle between 1 and 8 according to one embodiment of the invention.

PCR was performed using a thermal cycler which holds up to 96 reaction samples in a thermal cycling block in wells of a PCR sample plate. All 96 wells contained the same sample. The adaptive baseline algorithm was applied to calculate the PCR amplification. The starting cycle was limited to be a cycle between cycle 1 and 8. In these tests, all wells should detect the amplicon at the same cycle, and the amplification plots should all coincide. FIGS. 11A and 11B show the results from a typical uniformity run. FIG. 11A shows the result when the data were analyzed when the starting cycle was not limited to a cycle between 1 and 8, whereas FIG. 11B shows the result from the same data when the 1 to 8 cycle limit is applied to the start cycle determination. The 1 to 8 cycle limit not only decreases the spread of the data, it also reduces the incidence of artificially spurious results, as seen by the elimination of the two samples in FIG. 11A.

Variations, modifications, and other implementations of what is described herein will occur to those of ordinary skill in the art without departing from the spirit and scope of the invention as described and claimed herein.

All of the references identified hereinabove, including patents and patent applications, are hereby expressly incorporated herein by reference to the extent that they describe, set forth, provide a basis for or enable compositions and/or systems which may be important to the practice of one or more embodiments of the present inventions.

The invention claimed is:

1. A method for determining an absolute or relative quantity of a target nucleic acid in a sample, which includes calculating a baseline for a plurality of sample wells in a sample block cycling through cycles of a PCR reaction, said method comprising:
    (a) detecting an actual optical signal in a well containing the sample during a PCR reaction;
    (b) plotting the intensity of said actual optical signal observed in said well as a function of cycle number for said well to obtain a first plot;
    (c) automatically determining from said first plot a starting cycle and an ending cycle for said well, wherein the ending cycle is a last cycle before the target nucleic acid becomes detectable during the PCR reaction and the starting cycle is a first cycle after initial variability of the amplification reaction subsides, the first cycle being before the ending cycle;
    (d) determining a best fit line to points between and including the starting and ending cycle;
    (e) performing steps (a)-(d) independently for each of said plurality of wells;
    (f) calculating said baseline independently for each of said wells using the respective best fit line;
    (g) generating a working curve independently for each of said wells by subtracting the respective baseline from the respective first plot; and
    (h) using the at least one working curve to detect a corresponding amplified target nucleic acid.

2. The method of claim 1, wherein the step (c) of determining said starting cycle and ending cycle comprises obtaining 3-point moving average of the intensity of actual signals obtained for each cycle starting from cycle 2 and plotting said 3-point moving average as a function of cycle number starting from cycle 2 to obtain a second plot.

3. The method of claim 2, further comprising identifying a Cycle X from said first or second plot, wherein said Cycle X has a maximum change of slope from its previous cycle and has four immediately subsequent cycles, each of which has an increased slope compared to its previous cycle.

4. The method of claim 3, wherein Cycle X is identified within the first 8 cycles of said PCR reaction and an ending cycle is identified which is three cycles, or two cycles, or one cycle before said Cycle X.

5. The method of claim 3, wherein Cycle X is not identified within first 8 cycles of the PCR reaction and Cycle X is assigned as the ending cycle.

6. The method of claim 3, wherein said starting cycle is selected from the group consisting of: a first cycle which shows a different slope trend from its previous cycle; a cycle having a positive slope which is greater than the slope of its previous cycle; and a cycle having a slope less than 10% of an initial slope.

7. The method of claim 3, wherein said starting cycle is limited to a cycle between cycle 1 and 8.

8. The method of claim 1, wherein said best-fit line is calculated using a standard least root-mean-square-error algorithm:

$$rmse = \sqrt{\frac{\sum_{i=S}^{E}(m \times i + b) - y_i}{N}}$$

wherein N is the number of cycles between said starting and said ending cycles; S is said starting cycle; F is said ending cycle; $y_i$ is a signal of an $i^{th}$ cycle; and m and b are parameters of said best fit line.

9. The method of claim 1, wherein at least one of said wells comprises a sample suspected of containing a template nucleic acid and said optical signal is from a labeled probe specific for said nucleic acid.

10. The method according to claim 9, further comprising the step of subtracting said baseline calculated for said at least one of said wells from said first plot plotted for said at least one well to generate an adapted signal plot.

11. The method of claim 10, further comprising comparing said adapted signal plot to a standard plot generated from actual optical signal observed in a well as a function of cycle number recorded from a PCR reaction comprising a known amount of said template wherein said standard plot has been adjusted to remove a baseline calculated from said well comprising said known amount of template.

12. The method according to claim 11, wherein said comparing is used to determine the amount of said template.

13. The method of claim 9, wherein said label is a fluorescent label.

14. The method according to claim 9, wherein said sample is within a tube within said well.

15. A computer readable medium comprising program instructions for performing the method according to claim 1.

16. A system for calculating a baseline of a PCR reaction and using the baseline to determine an absolute or relative quantity of a target nucleic acid in a sample, said system comprising an analyzing device comprising a memory for implementing the program instructions of the computer-readable medium of claim 15.

17. The system according to claim 16, wherein said system further comprises a thermocycler for receiving said sample block, an input device for collecting optical signals from said sample wells, and an output device for displaying data obtained or generated by the analyzing device.

18. The system according to claim 17, wherein said output device is a computer.

19. A system of calculating a baseline of a PCR reaction, said system comprising an analyzing device comprising a memory for implementing program instructions of a computer-readable medium, wherein said program instructions comprise:

(a) plotting the intensity of the actual optical signal observed in a well as a function of cycle number for that well to obtain a first plot;

(b) automatically determining from said first plot a starting cycle after initial variability of the amplification reaction subsides and an ending cycle before the target nucleic acid becomes detectable during the PCR reaction for said well;

(c) determining a best fit line to the points between and including said starting and ending cycles;

(d) determining the baseline for said well using said best fit line;

(e) performing steps (a)-(d) independently for each of said plurality of wells; and (f) using said baseline to generate at least one working curve.

20. A method as recited in claim 1, further comprising the step of using the at least one working curve to quantify a starting molar concentration of the corresponding amplified target nucleic acid.

21. A method as recited in claim 1, further comprising the step of using the at least one working curve and a standard curve of molar concentrations as a function of cycle number to quantify a molar concentration of the corresponding amplified target nucleic acid.

22. A method as recited in claim 1, further comprising the step of using the at least one working curve and at least one working curve from a second sample to quantify a relative molar concentration of the corresponding amplified target nucleic acid between the samples.

* * * * *